(12) United States Patent
Abdel-Rahman

(10) Patent No.: US 6,490,938 B1
(45) Date of Patent: Dec. 10, 2002

(54) INTERNALLY PURGED GAS INJECTOR

(75) Inventor: Mahmoud F. Abdel-Rahman, Newark, DE (US)

(73) Assignee: Agilent Technologies, Inc., Palo Alto, CA (US)

( * ) Notice: Subject to any disclaimer, the term of this patent is extended or adjusted under 35 U.S.C. 154(b) by 0 days.

(21) Appl. No.: 09/956,882

(22) Filed: Sep. 21, 2001

(51) Int. Cl.$^7$ .................................................. G01N 1/00
(52) U.S. Cl. .................................................. 73/863.72
(58) Field of Search ..................... 73/863.71–863.73, 73/864.83, 864.84, 23.41, 23.42; 422/103

(56) References Cited

U.S. PATENT DOCUMENTS 3,330,150 A * 7/1967 Loyd et al. ................. 73/23.42
4,177,677 A * 12/1979 Ruzicka et al. ........... 73/863.71

* cited by examiner

Primary Examiner—Robert Raevis

(57) ABSTRACT

A gas injector comprises (1) a carrier gas channel through which a carrier gas can enter the injector, (2) an output channel through which the carrier gas and a gaseous sample can be injected from the device to an analytical instrument, (3) a sample gas channel capable of holding the gaseous sample, and (4) a switch structure regulating the connections among the sample gas channel, the carrier gas channel and the output channel. The injector also comprises at least a purge channel through which the carrier gas can flow across part of the device, purging therein and preventing contaminants from reaching the output channel. The gas injector provides a low baseline noise and a high signal to noise ratio when applied to a sensitive analytical instrument.

20 Claims, 12 Drawing Sheets

Comparative Sample

Comparative Sample

INTERNALLY PURGED GAS INJECTOR

BACKGROUND OF THE INVENTION

1. Field of the Invention

This invention relates to a gas injector which provides an improved signal to noise ratio when applied to a sensitive analytical instrument.

2. Description of the Related Art

The carrier gas that passes through a conventional gas injector can be contaminated easily due to air leaks or gases emitting from polymers and other internal surfaces of the injector. The contaminated carrier gas creates a high baseline noise when injected into a sensitive analytical instrument, therefore reducing the signal to noise ratio. Examples of sensitive analytical instruments include, but are not limited to, gas chromatographs, mass spectrometers or ion mobility spectrometers.

FIGS. 1 and 2 illustrate how the carrier gas becomes contaminated when passing through a conventional gas injector. The gas injector in FIGS. 1 and 2 comprises a six-port switching valve which has, in the clockwise order, ports 1, 2, 3, 4, 5 and 6. In FIG. 1, the switching valve is at the sample loading position. The carrier gas can flow through ports 1 and 2 to an analytical instrument. At the same time, a gaseous sample can be loaded to a sample gas channel through ports 5 and 6. The waste in the sample gas channel can be driven out of the sample gas channel through ports 3 and 4. Air leaks through the seals of ports 1 and 2, as well as gases emitting from the internal surfaces of the injector, contaminate the carrier gas when the carrier gas flows through the injector. The contaminated carrier gas enters the analytical instrument and creates a high baseline noise.

FIG. 2 shows the conventional gas injector at the sample injecting position. The carrier gas can be directed through, in the consecutive order, port 1, port 6, the sample gas channel, port 3 and port 2 to the analytical instrument, sweeping the gaseous sample in the sample gas channel to the analytical instrument.

Traditionally, contaminations by air leaks can be reduced by enclosing the gas injector in a container purged with the same type of gas as the carrier gas. Contaminations by the internally released gases can be minimized by limiting the upper temperature at which the gas injector operates.

Accordingly, there is a need to provide a gas injector which does not require externally purged enclosure and which is easy to make and use. There is also a need to make a gas injector which can operate at high upper temperatures and has a low baseline noise.

SUMMARY OF THE INVENTION

It is therefore an object of the present invention to produce a gas injection device which has a low baseline noise and a high signal to noise ratio.

It is another object of the invention to make a gas injection device which does not require externally purged enclosure and can be used at high upper temperatures without losing the high signal to noise ratio.

It is further an object of the invention to make a gas injection device which is easy to make and use.

In accordance with one aspect of the invention, the gas injection device comprises (1) a carrier gas channel through which a gas is capable of entering the device, (2) an output channel through which the gas can leave the device, (3) a first purge channel, (4) a sample gas channel capable of holding a gaseous sample and (5) a switch structure. The switch structure can be a multi-port switching valve, or an assembly of discrete switches such as pneumatic switches. Other flow controlling devices or switching mechanism can also be used as a switch structure, as appreciated by one of skill in the art. The switch structure has at least a first position and a second position. When the switch structure is at the first position, the carrier gas channel connects to the output channel through the sample gas channel and the first purge channel. When the switch structure is at the second position, the sample gas channel disconnects to the carrier gas channel, the output channel and the first purge channel, and the carrier gas channel connects to (1) a first vent environment through the first purge channel and (2) the output channel.

In accordance with another aspect of the invention, the gas injection device further comprises a second purge channel and a connecting channel. The carrier gas channel connects to the output channel through the connecting channel. When the switch structure is at the first position, the carrier gas channel also connects to the output channel through, in the consecutive order, the first purge channel, the sample gas channel and the second purge channel. When the switch structure is at the second position, the sample gas channel disconnects to the carrier gas channel, and the carrier gas channel connects to a second vent environment through, in the consecutive order, the connecting channel and the second purge channel.

In accordance with yet another aspect of the invention, the gas injection device comprises a first vent channel and a second vent channel. When the switch structure is at the second position, the carrier gas channel connects to the first vent environment through, in the consecutive order, the first purge channel and the first vent channel, and the carrier gas channel connects to the second environment through, in the consecutive order, the connecting channel, the second purge channel and the second vent channel. When the switch structure is at the first position, the carrier gas channel disconnects to the second vent channel, and preferably, the carrier gas channel disconnects to both the first and the second vent channels.

In one embodiment of the invention, the pneumatic restriction of the connecting channel is greater than the sum of the pneumatic restrictions of the first purge channel, the sample gas channel and the second purge channel.

In another embodiment of the invention, the first and the second vent environments are the atmosphere.

In a preferred embodiment of the invention, the switch structure of the gas injection device comprises a 8-port switching valve comprising, in the clockwise order, ports 1, 2, 3, 4, 5, 6, 7 and 8. When the switch structure is at the first position, the carrier gas channel connects to the output channel through, in the consecutive order, the first purge channel, port 7, port 6, the sample gas channel, port 3, port 2 and the second purge channel. When the switch structure is at the second position, the carrier gas channel connects to the first vent environment through, in the consecutive order, the first purge channel, port 7, port 8 and the first vent channel, and the carrier gas channel connects to the second vent environment through, in the consecutive order, the connecting channel, the second purge channel, port 2, port 1 and the second vent channel.

In another preferred embodiment, the switch structure comprises a 6-port switching valve. When the switch structure is at the first position, the carrier gas channel connects to the output channel through, in the consecutive order, the first purge channel, port 5, the sample gas channel, port 2 and the second purge channel. When the switch structure is at the second position, the carrier gas channel connects to the first vent environment through, in the consecutive order, the first purge channel, port 5, port 6 and the first vent channel, and the carrier gas channel connects to the second vent environment through, in the consecutive order, the connecting channel, the second purge channel, port 2, port 1 and the second vent channel.

In accordance with another aspect of the invention, the switch structure comprises three pneumatic switches. When the switch structure is at the first position, the carrier gas channel connects to the output channel through, in the consecutive order, the first purge channel, the first pneumatic switch, the sample gas channel, the second pneumatic switch and the second purge channel, and the second purge channel disconnects to the second vent environment. When the switch structure is at the second position, the carrier gas channel disconnects to the sample gas channel, and the carrier gas channel connects to the second vent environment through, in the consecutive order, the connecting channel, the second purge channel, the third pneumatic switch and the second vent channel.

In accordance with yet another aspect of the invention, the output channel connects to an analytical instrument. The analytical instrument may be a gas chromatography, a mass spectrometer or an ion mobility spectrometer.

In accordance with one aspect of the invention, a method is provided for introducing a gaseous sample to an analytical device. The method comprises the steps of (a) directing a carrier gas to the first vent environment through, in the consecutive order, the carrier gas channel and the first purge channel, and directing the gaseous sample to the sample gas channel, wherein the switch structure is at the second position; and (b) changing the switch structure from the second position to the first position and directing the carrier gas to the output channel through, in the consecutive order, the carrier gas channel and the sample gas channel.

In accordance with another aspect of the invention, the method for introducing a gaseous sample to an analytical instrument comprises the steps of: (a) directing a carrier gas to the first vent environment through, in the consecutive order, the carrier gas channel and the first purge channel, directing the carrier gas to the second vent environment through, in the consecutive order, the carrier gas channel, the connecting channel and the second purge channel, and directing the gaseous sample to the sample gas channel, wherein the switch structure is at the second position; and (b) changing the switch structure from the second position to the first position and directing the carrier gas to the output channel through, in the consecutive order, the carrier gas channel, the first purge channel, the sample gas channel and the second purge channel.

In accordance with yet another aspect of the invention, the method for introducing a gaseous sample to an analytical instrument comprises the steps of: (a) directing a carrier gas to the first vent environment through, in the consecutive order, the carrier gas channel, the first purge channel and the first vent channel, directing the carrier gas to the second vent environment through, in the consecutive order, the carrier gas channel, the connecting channel, the second purge channel and the second vent channel, and directing the gaseous sample to the sample gas channel, wherein the switch structure is at the second position; and (b) changing the switch structure from the second position to the first position and directing the carrier gas to the output channel through, in the consecutive order, the carrier gas channel, the first purge channel, the sample gas channel and the second purge channel.

In one embodiment, the gas injection device comprises an input means for channeling a gas into the device, an output means for channeling the gas out of the device, a first purge channel, a holding means for holding a gaseous sample, and a switching means for regulating connections among the holding means, the input means and the output means. The switching means has at least an open state and a close state. When the switching means is at the open state, the gas is capable of being channeled from the input means through the first purge channel and the holding means to the output means. When the switching means is at the close state, the holding means disconnects to the input means and the output means, and the gas is capable of being channeled to (1) a first vent environment through, in the consecutive order, the input means and the first purge channel and (2) the output means through the input means.

In another embodiment, the device further comprises a second purge channel and a connecting means for connecting the input means to the output means. When the switching means is at the open state, the gas is capable of being channeled through, in the consecutive order, the input meaning, the first purge channel, the holding means and the second purge channel to the output means. When the switching means is at the close state, the holding means disconnects to the input means, and the gas is capable of being channeled through, in the consecutive order, the input means, the connecting means and the second purge channel to a second vent environment.

In a preferred embodiment, the pneumatic restriction of the connecting means is greater than the sum of the pneumatic restrictions of the first purge channel, the holding means and the second purge channel.

In accordance with a further aspect of the invention, the switch structure of the gas injection device of the invention comprises a first switch and a second switch. When the switch structure is at the first position, the carrier gas channel connects to the output channel through, in the consecutive order, the first switch, the sample gas channel and the second switch. In one embodiment, the switch structure comprises a switching valve which comprises a plurality of ports. Each of the first and the second switches comprises at least one of said plurality of ports.

DESCRIPTION OF THE EMBODIMENTS

The gas injection device of the invention comprises a pneumatic structure and a sample loading structure. A switch structure regulates the connection between the pneumatic structure and the sample loading structure. The pneumatic structure channels a carrier gas to the switch structure, purging the switch structure and therefore reducing contaminations by air leaks through the switch structure. The carrier gas channeled by the pneumatic structure also purges the internal surfaces of the injection device to minimize contaminations by internally released gases. These features provide the gas injection device of the invention with a lower baseline noise and a higher signal to noise ratio, as compared to a conventional gas injector. These features also allows the injection device to operate at high upper temperatures without losing the high signal to noise ratio. In addition, because the injection device of the invention purges internally, it consumes less amount of carrier gas than a conventional gas injector which purges externally. Moreover, the injection device of the invention does not require an externally purged enclosure, and therefore has a lower manufacturing cost and a better reliability than a conventional gas injector.

Figure 1:
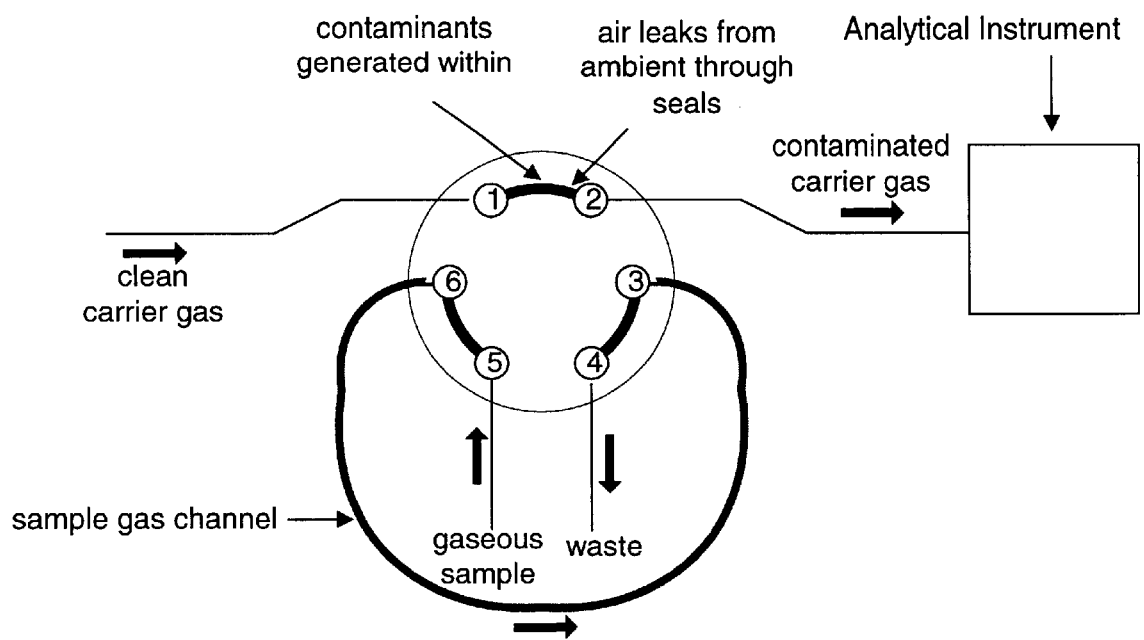
FIG. 1 illustrates a conventional gas injector comprising a 6-port switching valve, wherein the conventional gas injector is at the sample loading position.
Figure 2:
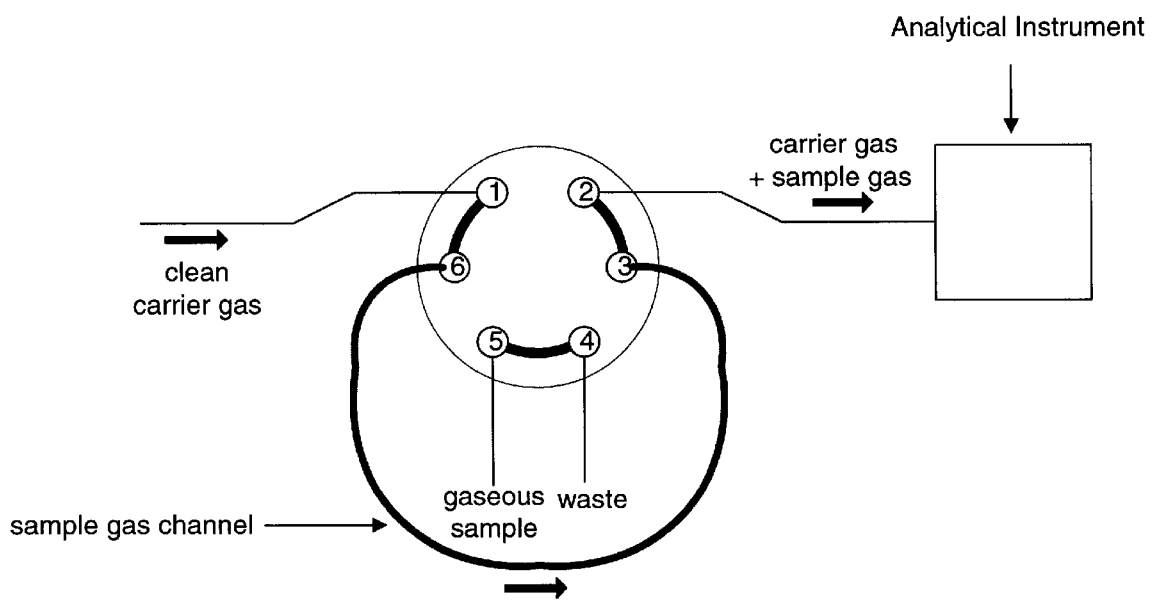
FIG. 2 illustrates the conventional gas injector of FIG. 1, wherein the conventional gas injector is at the sample injecting position.
Figure 3:
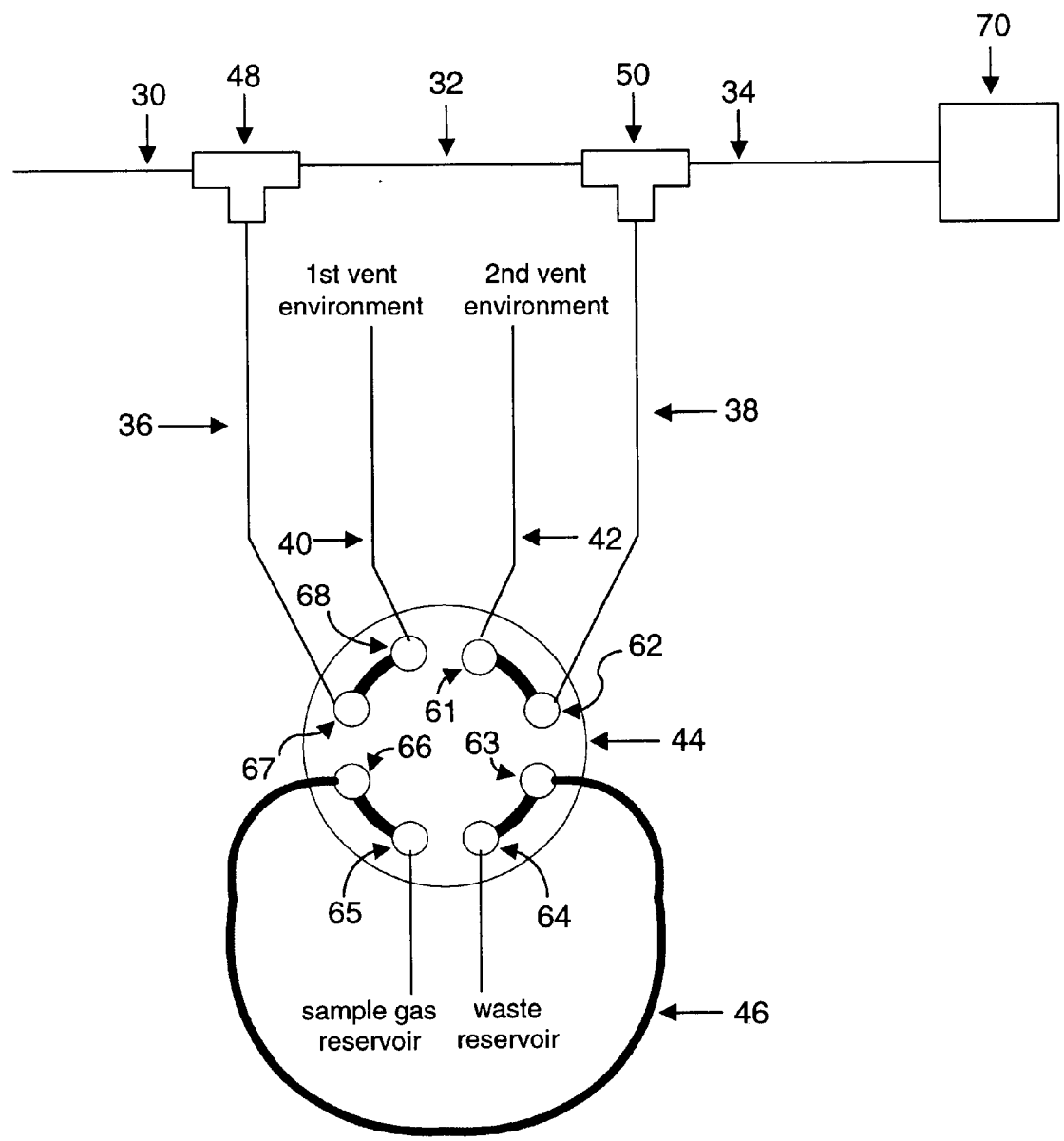
FIG. 3 shows a gas injection device of the invention which comprises a 8-port switching valve, wherein the injection device is at the sample loading position.
Figure 4:
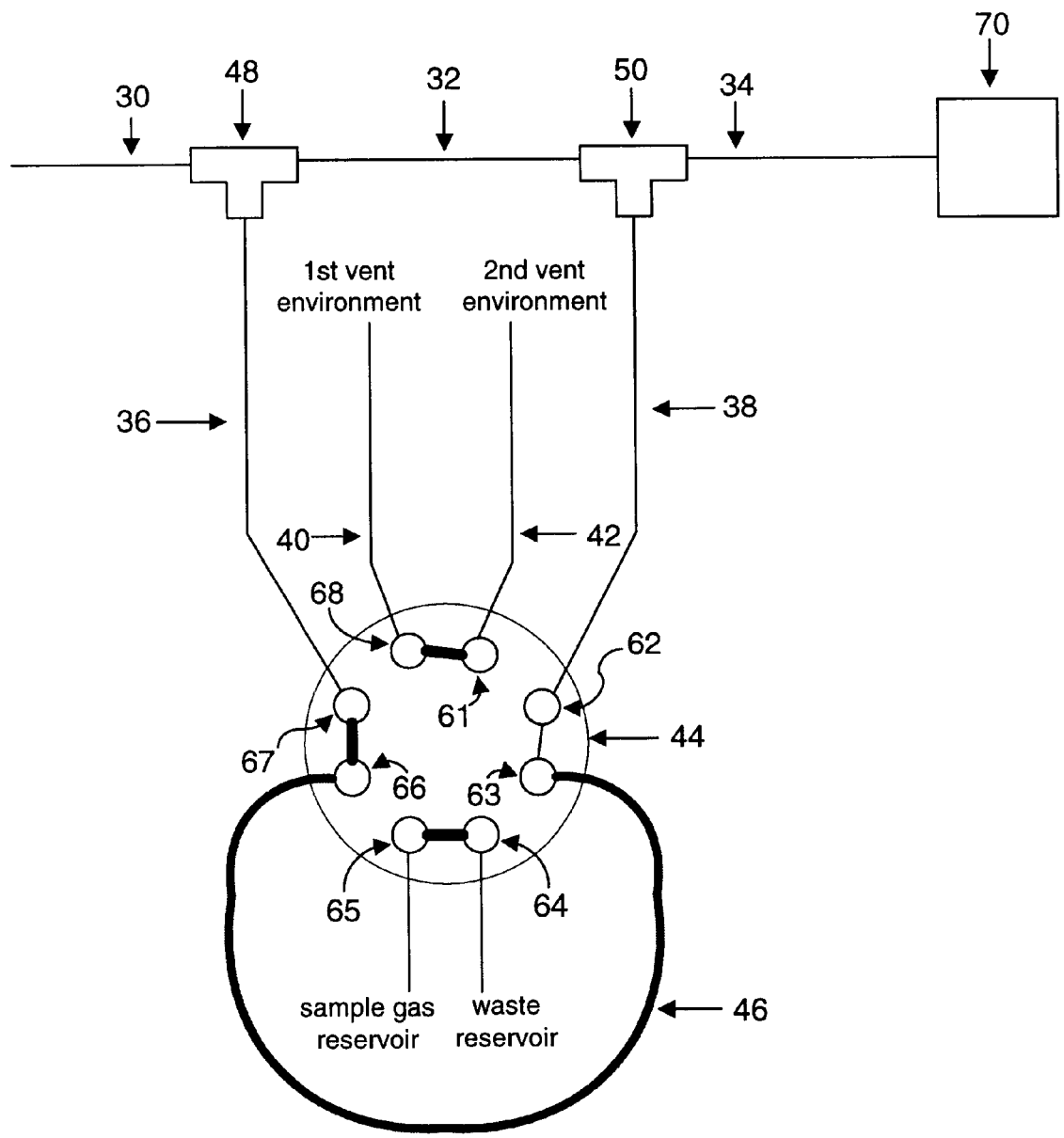
FIG. 4 shows the injection device of FIG. 3 at the sample injecting position.

FIGS. 3 and 4 depict one embodiment of the invention. The pneumatic structure comprises a carrier gas channel 30, which connects to an output channel 34 through a connecting channel 32. The carrier gas channel also connects to a first purge channel 36. The carrier gas channel 30 comprises an opening through which the carrier gas can be directed into the gas injection device. The output channel 34 comprises an opening through which the carrier gas or a sample gas can be channeled out of the device. Preferably, the output channel 34 further connects to an analytical instrument 70, which may be a gas chromatography, a mass spectrometer or an ion mobility spectrometer. The carrier gas or the sample gas that comes out of the device can be directed to the analytical instrument 70 for further analysis.

Preferably, a T-connector 48 is used to connect the carrier gas channel 30, the first purge channel 36 and the connecting channel 32. The first opening of the T-connector 48 can be used as or connect immediately to the carrier gas channel 30. The second opening of the T-connector 48 connects immediately to the purge channel 36. The third opening of the T-connector 48 connects immediately to the connecting channel 32. A preferred type of T connector is the zero-volume T-type pneumatic connector. Likewise, a T-connector 50 can be used to connect the connecting channel 32, the output channel 34 and a second purge channel 38.

The first purge channel 36 connects to a first vent environment. The second purge channel 38 connects to a second vent environment. An example of a suitable vent environment is the atmosphere. Preferably, the device also comprises a first vent channel 40 and a second vent channel 42. The first vent channel 40 is positioned between the first vent environment and the first purge channel 36, and the second vent channel 42 is positioned between the second vent environment and the second purge channel 38. The switch structure of the device comprises a 8-port switching valve 44 which regulates the connection between the first purge channel 36 and the first vent channel 40. The switching valve 44 also controls the connection between the second purge channel 38 and the second vent channel 42.

The sample loading structure comprises a sample gas channel 46 capable of holding a gaseous sample. The sample gas channel 46 has two openings. One opening connects to a sample gas reservoir, and the other opening connects to a waste reservoir. The switching valve 44 regulates the connections between the sample gas channel 46 and the sample gas/waste reservoirs.

The switching valve 44 comprises, in the clockwise order, port 61, port 62, port 63, port 64, port 65, port 66, port 67 and port 68. Ports 66 and 67 regulate the connection between the first purge channel 36 and the sample gas channel 46, and therefore functions as a switch. Ports 62 and 63 controls the connection between the sample gas channel 46 and the second purge channel 38, and thus also functions as a switch. As used herein, a "switch" refers to any structure which has at least a first state and a second state and can regulate a connection between two channels. When the switch is at the first state, the two channels can connect to each other through the switch. When the switch is at the second state, the two channels do not connect to each other through the switch.

The 8-port switching valve 44 has at least a sample loading and a sample injecting position. FIG. 3 illustrates when the 8-port switching valve is at the sample loading position. At the sample loading position, the carrier channel 30 disconnects to the sample gas channel 46. The carrier channel 30 connects to the first vent environment through, in the consecutive order, the first purge channel 36, port 67, port 68 and the first vent channel 40. The carrier channel connects to the second vent environment through, in the consecutive order, the connecting channel 32, the second purge channel 38, port 62, port 61 and the second vent channel 42. Accordingly, the carrier gas can flow through, in the consecutive order, the carrier gas channel 30, the first purge channel 36, port 67, port 68 and the first vent channel 40 to the first vent environment. The carrier gas can flow to the second vent environment through, in the consecutive order, the connecting channel 32, the second purge channel 38, port 62, port 61 and the second vent channel 42. In addition, the carrier gas can flow from the carrier gas channel 30 through the connecting channel 32 to the output channel 34. Preferably, the carrier gas that flows to the first and the second vent environments are kept to a minimum amount so as to be just sufficient to prevent contaminants from diffusing to the carrier gas channel 30 and the output channel 34. This may be achieved by adjusting the pneumatic restrictions of the first purge channel 36, the first vent channel 40, the second purge channel 38 and the second vent channel 42, as appreciated by one of skill in the art.

At the sample loading position, the sample gas channel 46 disconnects to ports 61–62 and ports 67–68, but connects to ports 63–66. A gaseous sample can be loaded through, in the consecutive order, port 65 and port 66 into the sample gas channel 46. The waste or excessive gaseous sample can be driven out of the sample gas channel 46 through, in the consecutive order, port 63 and port 64.

FIG. 4 shows the switching valve 44 at the sample injecting position. Ports 61, 64, 65 and 68 disconnect to the carrier gas channel 30, the output channel 34, the sample gas channel 46, the first purge channel 36 and the second purge channel 38. The carrier gas channel 30 and the sample gas channel 46 disconnect to the first and the second vent environment. The carrier gas channel 30 connects through, in the consecutive order, the first purge channel 36, port 67 and port 66 to the sample gas channel 46, which in turn connects through, in the consecutive order, port 63, port 62 and the second purge channel 38 to the output channel 34. Thus, the carrier gas can be directed through, in the consecutive order, the carrier gas channel 30, the first purge channel 36, port 67, port 66, the sample gas channel 46, port 63, port 62 and the second purge channel 38 to the output channel 34, driving the gaseous sample in the sample gas channel 46 to the output channel 34. The carrier gas channel 30 also connects to the output channel 34 through the connecting channel 32, allowing the carrier gas to flow from the carrier gas channel 30 through the connecting channel 32 to the output channel 34. The output channel 34 may further connect to an analytical instrument 70.

In a preferred embodiment, the pneumatic restriction of the connecting channel 32 is greater than the sum of the pneumatic restrictions of the first purge channel 36, the sample gas channel 46 and the second purge channel 38. Consequently, the carrier gas flowing through the connecting channel 32 to the output channel 34 does not significantly broaden the gaseous sample peak that is driven to the output channel 34 by the carrier gas flowing through, in the consecutive order, the carrier gas channel 30, the first purge channel 36, the sample gas channel 46 and the second purge channel 38 to the output channel 34. As appreciated by one of skill in the art, the pneumatic restriction of a channel represents the ratio of the pressure drop along the channel to the gas flow rate in the channel.

The connections between the components of the injection device are preferably with excellent seals to minimize potential air leaks. All tubes, connectors, channels and switches used in the invention are preferably made of clean materials, such as metallic alloys or stainless steel.

In a preferred embodiment, the connecting channel 30, the first purge channel 36, the first vent channel 40, the second purge channel 38 and the second vent channel 42 are made of stainless steel tubes. The sample gas channel 46 is a stainless steel tube or a fused silica tube. The length of the connecting channel 32 is 0.05 meter (m), and the internal diameter of the connecting channel 32 is 0.1 millimeter (mm). The lengths of the first purge channel 36, the first vent channel 40, the sample gas channel 46, the second purge channel 38 and the second vent channel 42 are 0.1 m, 0.12 m, 0.12 m, 0.1 m and 0.12 m, respectively. The internal diameters of the first purge channel 36, the first vent channel 40, the sample gas channel 46, the second purge channel 38 and the second vent channel 42 are 0.32 mn, 0.05 mm, 0.32 mm, 0.32 mm and 0.05 mm, respectively.

Figure 5:
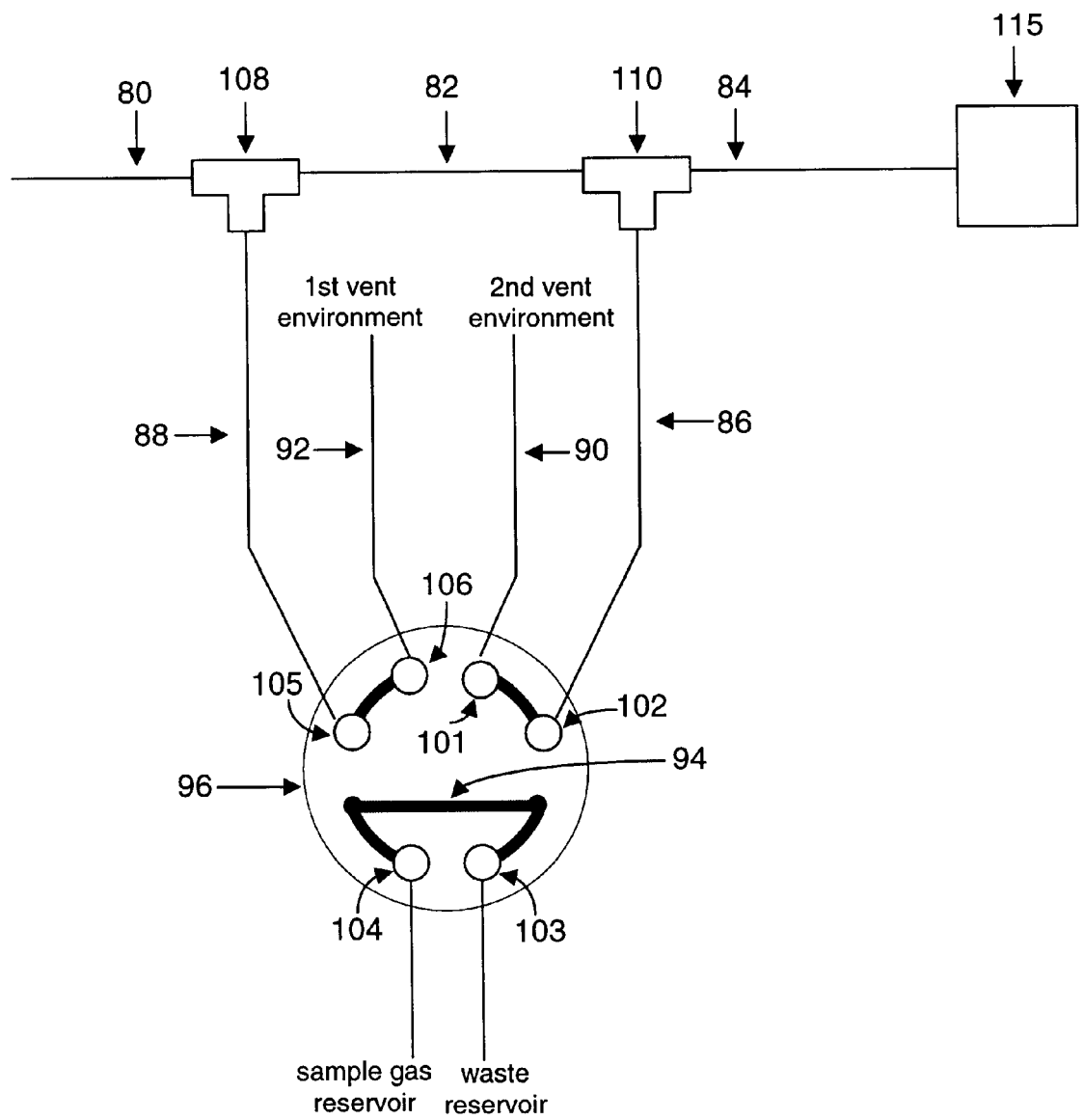
FIG. 5 depicts a gas injection device of the invention which comprises a 6-port switching valve, wherein the injection device is at the sample loading position.
Figure 6:
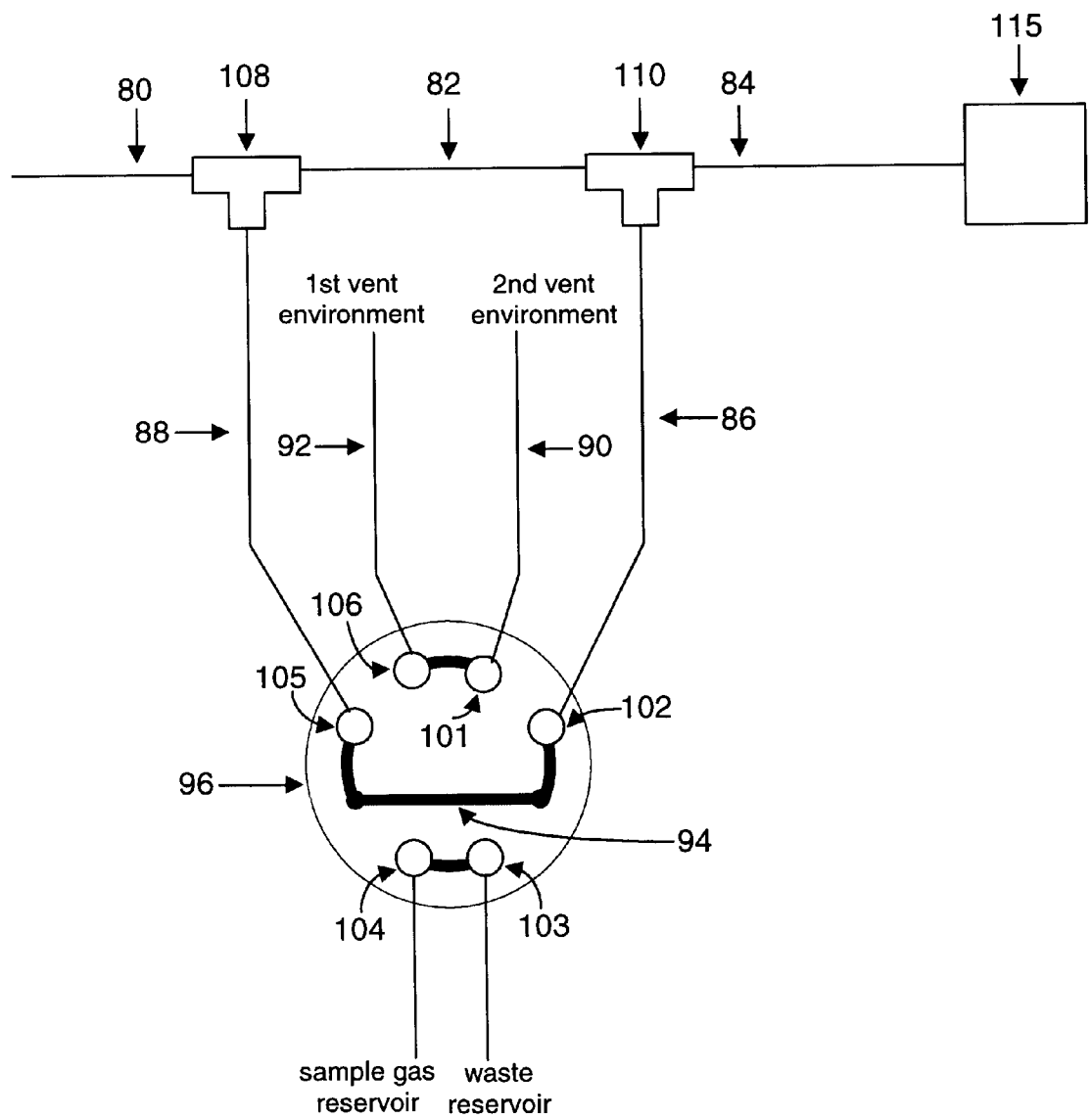
FIG. 6 depicts the injection device of FIG. 5 at the sample injecting position.

FIGS. 5–6 illustrate another embodiment. The switch structure comprises a 6-port switching valve 96. Preferably, the sample gas channel 94 is built within the 6-port switching valve 96. The switching valve 96 comprises, in the clockwise order, ports 101, 102, 103, 104, 105 and 106.

FIG. 5 shows the switching valve 96 at the sample loading position. The carrier gas channel 80 connects to a first vent environment through, in the consecutive order, the first purge channel 88, port 105, port 106 and the first vent channel 92. The carrier gas channel also connects to a second vent environment through, in the consecutive order, the connecting channel 82, the second purge channel 86, port 102, port 101 and the second vent channel 90. In addition, the carrier gas channel 80 connects to the output channel 84 through the connecting channel 82. The sample gas channel 94 connects to ports 103 and 104. A gaseous sample can be loaded to the sample gas channel 94 through port 104, and the waste or excessive gas can be swept out of the sample gas channel 94 through port 103.

FIG. 6 illustrates the switching valve 96 at the sample injecting position. Ports 101, 103, 104 and 106 disconnect to the sample gas channel 94, the carrier gas channel 80, the output channel 84, the first purge channel 88 and the second purge channel 86. The carrier gas channel 80 connects through, in the consecutive order, the first purge channel 88, port 105, the sample gas channel 94, port 102 and the second purge channel 86 to the output channel 84. The carrier gas channel 80 also connects to the output channel 84 through the connecting channel 82. The output channel 84 may connect to an analytical instrument 115.

Figure 7:
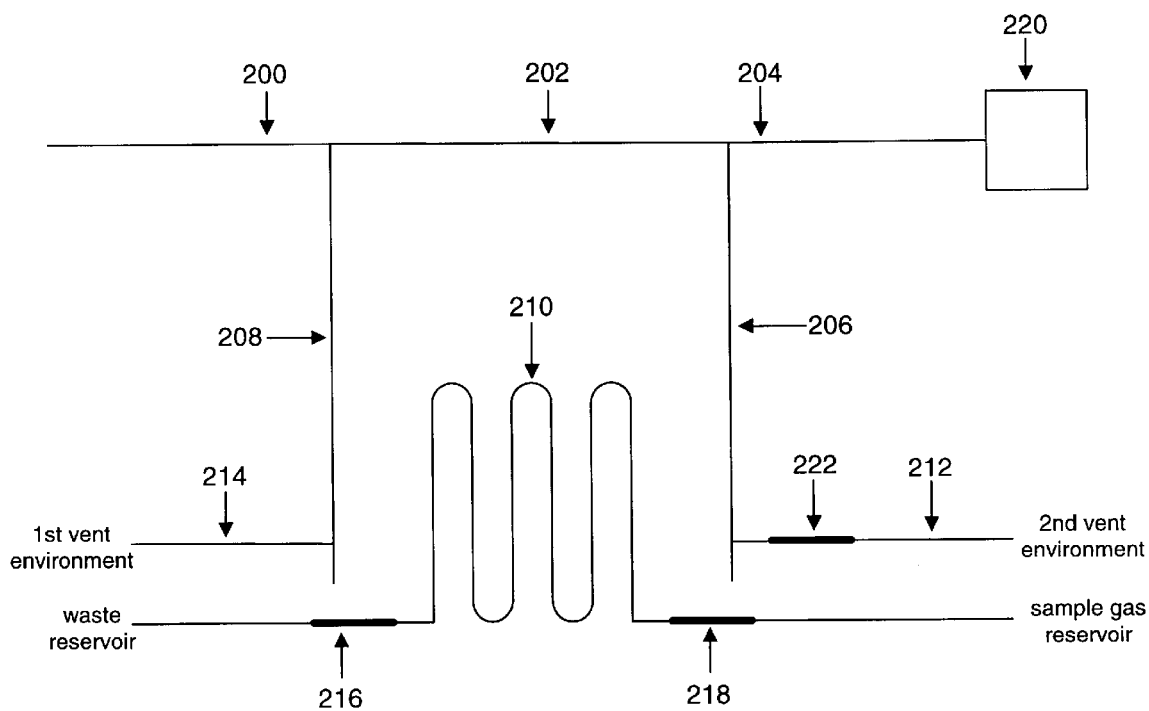
FIG. 7 illustrates a gas injection device comprising a set of discrete switches, wherein the injection device is at the sample loading position.
Figure 8:
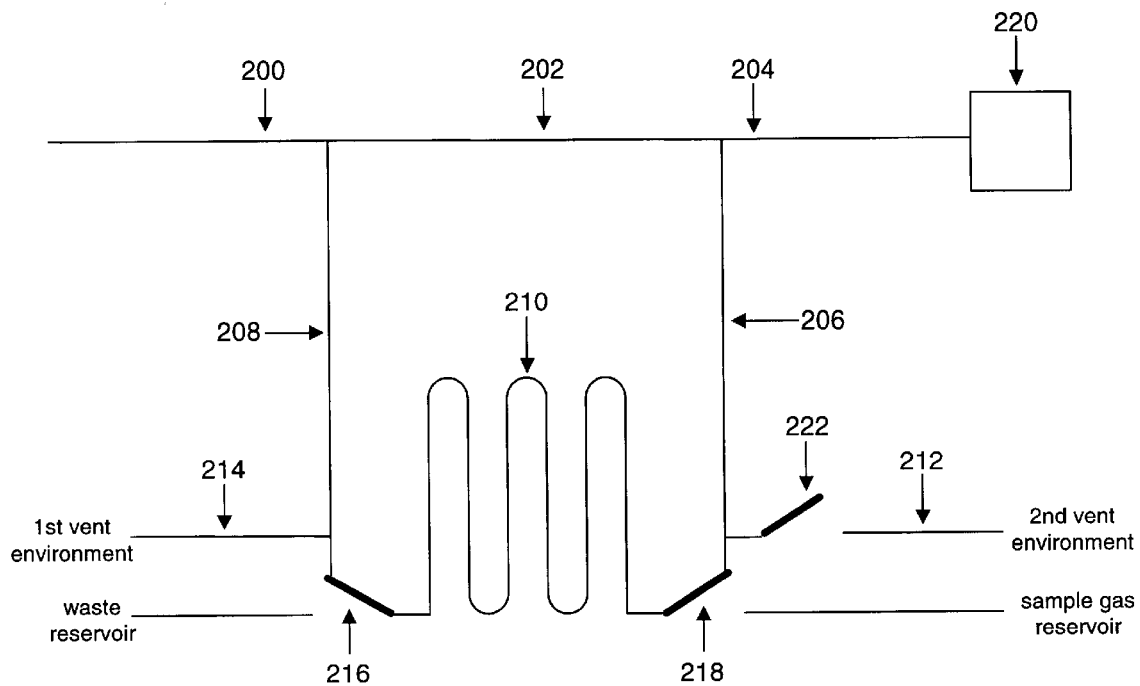
FIG. 8 illustrates the injection device of FIG. 7 at the sample injecting position.

In another preferred embodiment, as shown in FIGS. 7 and 8, the switch structure comprises a set of discrete switches. These discrete switches are preferably pneumatic switches, and may be remotely coupled by mechanic means, electronic means, or other means, as appreciated by one of skill in the art. The injection device of this embodiment can be built using silicon micromachining technology or similar technologies. The switch structure of this embodiment comprises three switches (216, 218 and 222). Switch 216 is a double-pole single throw switch, and positions between the first purge channel 208 and the sample gas channel 210. Switch 216 controls the connection between the sample gas channel 210 and the first purge channel 208. Switch 218 is also a double-pole single throw switch, and positions between the second purge channel 206 and the sample gas channel 210. Switch 218 regulates the connection between the sample gas channel 210 and the second purge channel 206. Switch 222 is a single-pole single throw switch, and regulates the connection between the second purge channel 206 and the second vent channel 212.

FIG. 7 shows the switch structure at the sample loading position. Switch 222 connects the second purge channel 206 to the second vent channel 212, and the second vent channel 212 in turn connects to the second vent environment. The sample gas channel 210 disconnects to the first purge channel 208 and the second purge channel 206. The sample gas channel 210 connects to the sample gas reservoir through switch 218, and connects to the waste reservoir through switch 216. The carrier gas channel 200 connects to the output channel 204 through the connecting channel 202. The carrier gas channel 200 also connects to the first vent environment through, in the consecutive order, the first purge channel 208 and the first vent channel 214. The carrier gas channel 200 further connects to the second vent environment through, in the consecutive order, the connecting channel 202, the second purge channel 206, switch 222 and the second vent channel 212.

FIG. 8 shows the switch structure at the sample injecting position. The second purge channel 206 disconnects to the second vent channel 212 and the second vent environment. The sample gas channel 210 connects to the first purge channel 208 through switch 216, and connects to the second purge channel 206 through switch 218. The sample gas channel 210 disconnects to the sample gas reservoir and the waste reservoir. The carrier gas channel 200 connects through, in the consecutive order, the first purge channel 208, switch 216, the sample gas channel 210, switch 218 and the second purge channel 206 to the output channel 204. The carrier gas channel 200 also connects to the output channel 204 through the connecting channel 202. The output channel 204 may connect to an analytical instrument 220.

Figure 9:
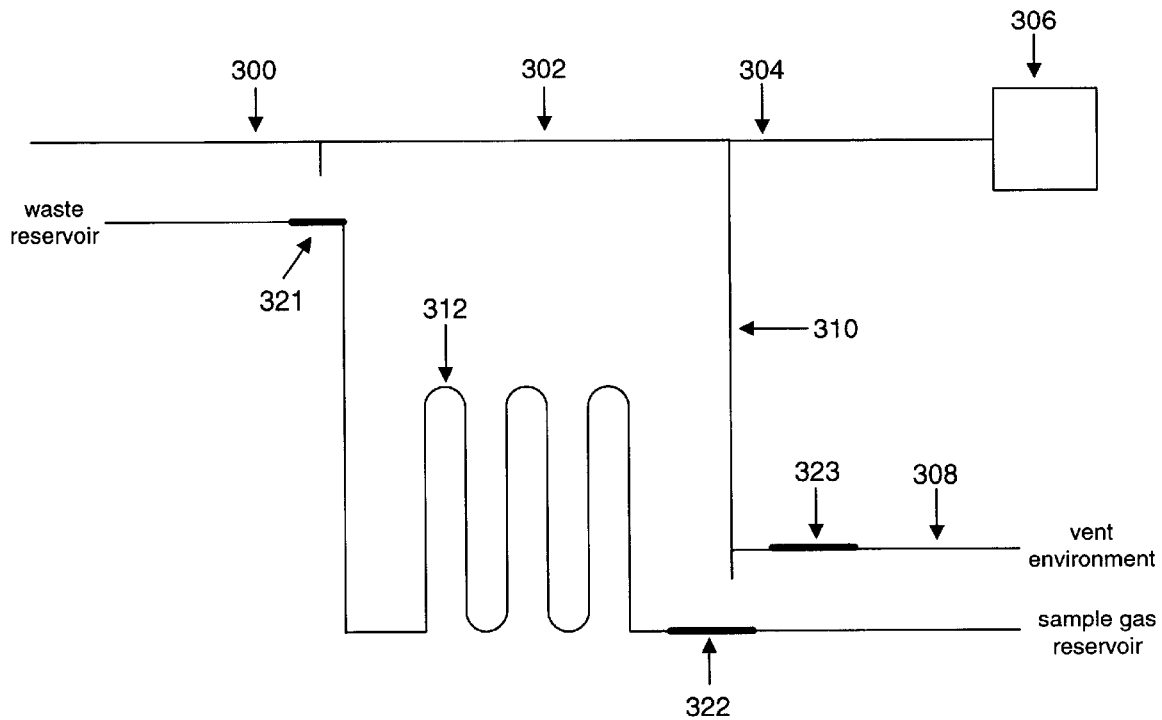
FIG. 9 shows a gas injection device that can channel only one purge flow, wherein the device is at the sample loading position.
Figure 10:
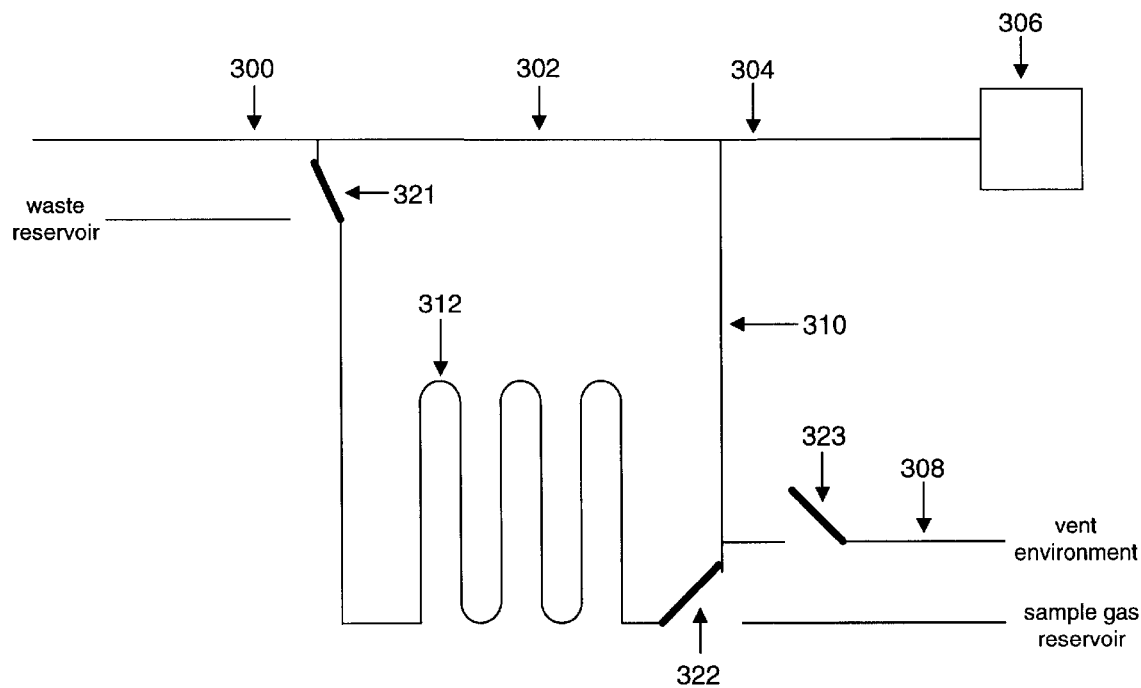
FIG. 10 is the gas injection device of FIG. 9 at the sample injecting position.

FIGS. 9 and 10 illustrate another embodiment, in which the injection device is capable of channeling only one purge flow. At the sample loading position, as depicted by FIG. 9, the carrier channel 300 disconnects to the sample gas channel 312. the carrier gas channel 300 connects to the output channel 304 through the connecting channel 302. The carrier gas channel 300 also connects to a vent environment through, in the consecutive order, the connecting channel 302, the purge channel 310, switch 323 and the vent channel 308. The sample gas channel 312 connects to a sample gas reservoir through switch 322, and to a waste reservoir through switch 321.

FIG. 10 shows the device at the sample injecting position. Switches 321 and 322 disconnect the sample gas channel 312 from the waste reservoir and the sample gas reservoir, respectively. Switch 321 connects the carrier gas channel 300 to the sample gas channel 312, and switch 322 connects the sample gas channel 312 to the purge channel 310. Accordingly, a carrier gas is capable of flowing through, in the consecutive order, the carrier gas channel 300, switch 321, the sample gas channel 312, switch 322 and the purge channel 310 to the output channel 304. The output channel 304 may further connect to an analytical instrument 306.

Figure 11:
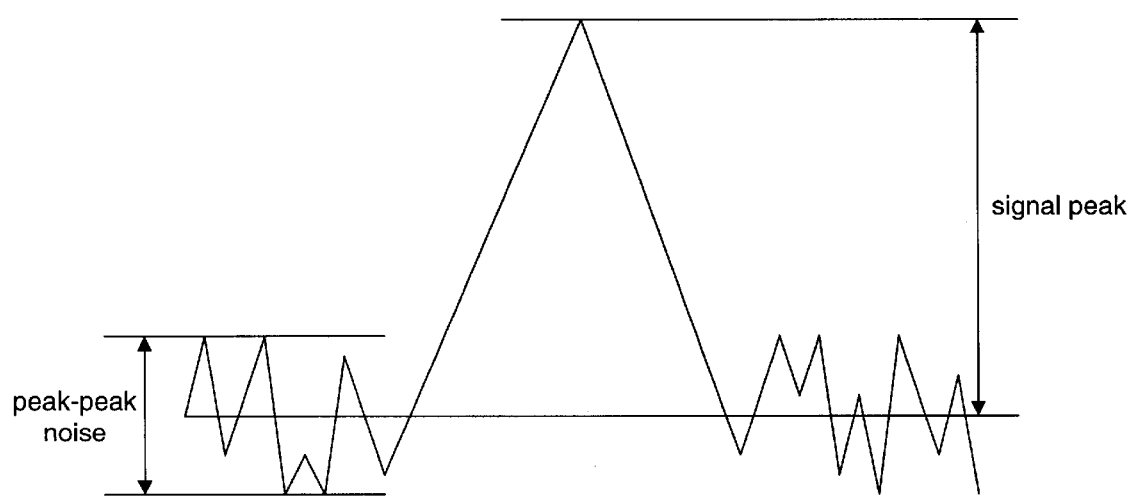
FIG. 11 shows the baseline noise peak and the gaseous sample output peak measured by a highly sensitive helium discharge ionization detector using a conventional gas injector.
Figure 12:
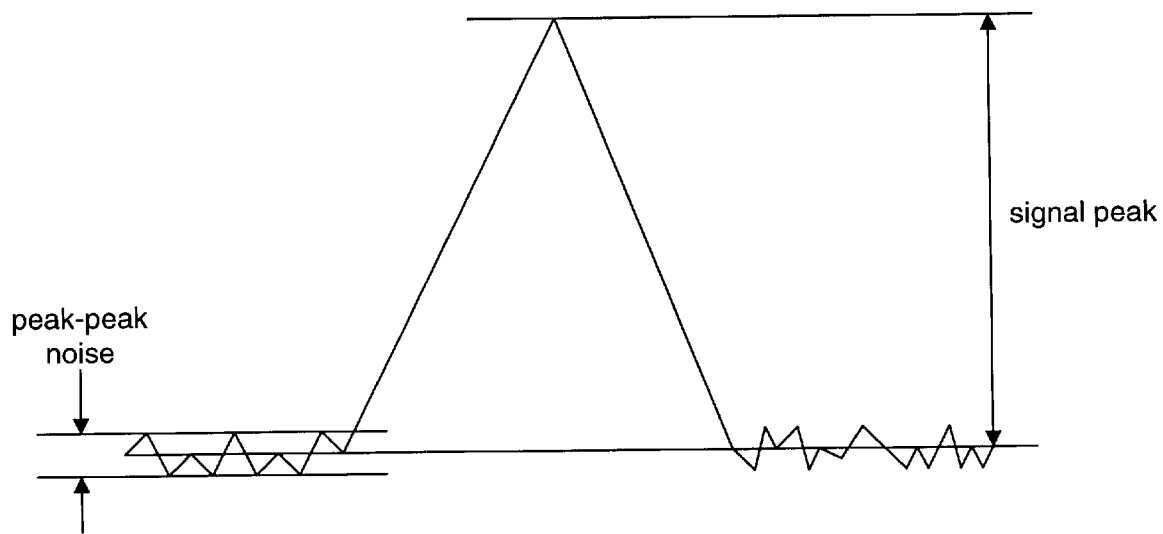
FIG. 12 displays the baseline noise peak and the gaseous sample output peak measured by the same analytical instrument of FIG. 1 1 but using a gas injection device of the invention.

FIG. 11 illustrates the baseline noise and the gaseous sample output peak measured by a highly sensitive helium discharge ionization detector when using a conventional gas injector. FIG. 12 displays the baseline noise and the gaseous sample output peak measured by the same analytical instrument when using the injection device of the invention as shown in FIGS. 3–4. Comparison of FIG. 11 to FIG. 12 demonstrates that the injection device of the invention significantly reduces the baseline noise and increases the signal to noise ratio.

As used herein, a "channel" refers to a structure through which a gas is capable of passing through. A hole structure, such as an opening of a T-connector, can be used as a channel. A first structure "connects" to a second structure if a gas in the first channel is capable of traveling or communicating to the second channel. A first structure "disconnects" to a second structure if a gas in the first structure is incapable to travel or communicate to the second structure. A first structure connects to a second structure through a third structure if a gas in the first structure is capable of traveling or communicating to the third structure, and then from the third structure to the second structure. A "vent environment" refers to a place into which the gas in a device can be released or vented. A typical vent environment is the atmosphere.

The present invention has been described in considerable details with reference to certain preferred embodiments thereof. However, the spirit and scope of the appended claims should not be limited to the description of these embodiments. All the features disclosed herein may be replaced by alternative features serving the same, equivalent or similar purposes, as appreciated by one of skill in the art.

What is claimed:

1. A device, comprising:
   a carrier gas channel;
   an output channel;
   a first purge channel;
   a sample gas channel capable of holding a gaseous sample; and
   a switch structure having at least a first position and a second position;
   wherein when the switch structure is at the first position, the carrier gas channel connects through the sample gas channel and the first purge channel to the output channel; and
   wherein when the switch structure is at the second position, the sample gas channel disconnects to the carrier gas channel, and the carrier gas channel connects to (1) a first vent environment through the first purge channel and (2) the output channel.

2. A method for providing a gaseous sample using the device according to claim 1, comprising the steps of:
   (a) directing a carrier gas through, in the consecutive order, the carrier gas channel and the first purge channel to the first vent environment, and directing the gaseous sample to the sample gas channel, wherein the switch structure is at the second position; and
   (b) directing the carrier gas through, in the consecutive order, the carrier gas channel and the sample gas channel to the output channel, wherein the switch structure is at the first position.

3. The device according to claim 1, further comprising:
   a second purge channel; and
   a connecting channel;
   wherein the carrier gas channel connects to the output channel through the connecting channel; wherein when the switch structure is at the first position, the carrier gas channel connects through, in the consecutive order, the first purge channel, the sample gas channel and the second purge channel to the output channel; and wherein when the switch structure is at the second position, the carrier gas channel connects through, in the consecutive order, the connecting channel and the second purge channel to a second vent environment.

4. A method for providing a gaseous sample using the device according to claim 3, comprising the steps of:
   (a) directing a carrier gas through, in the consecutive order, the carrier gas channel and the first purge channel to the first vent environment, directing the carrier gas through, in the consecutive order, the carrier gas channel, the connecting channel and the second purge channel to the second vent environment, and directing the gaseous sample to the sample gas channel, wherein the switch structure is at the second position; and
   (b) directing the carrier gas through, in the consecutive order, the carrier gas channel, the first purge channel, the sample gas channel and the second purge channel to the output channel, wherein the switch structure is at the first position.

5. The device according to claim 3, further comprising a first vent channel and a second vent channel, wherein when the switch structure is at the second position, the carrier gas channel connects through, in the consecutive order, the first purge channel and the first vent channel to the first vent environment, and the carrier gas channel connects through, in the consecutive order, the connecting channel, the second purge channel and the second vent channel to the second vent environment.

6. The device according to claim 5, wherein when the switch structure is at the first position, the carrier gas channel disconnects to the second vent channel.

7. A method for providing a gaseous sample using the device according to claim 6, comprising the steps of:
(a) directing a carrier gas through, in the consecutive order, the carrier gas channel, the first purge channel and the first vent channel to the first vent environment, directing the carrier gas through, in the consecutive order, the carrier gas channel, the connecting channel, the second purge channel and the second vent channel to the second vent environment, and directing the gaseous sample to the sample gas channel, wherein the switch structure is at the second position; and
(b) directing the carrier gas through, in the consecutive order, the carrier gas channel, the first purge channel, the sample gas channel and the second purge channel to the output channel, wherein the switch structure is at the first position.

8. The device according to claim 6, wherein the first and the second vent environments are the atmosphere.

9. The device according to claim 6, wherein the switch structure comprises a switching valve which comprises a first port, a second port, a third port, a fourth port, a fifth port, a sixth port, a seventh port and a eighth port;
wherein when the switch structure is at the first position, the carrier gas channel connects through, in the consecutive order, the first purge channel, the seventh port, the sixth port, the sample gas channel, the third port, the second port and the second purge channel to the output channel; and
wherein when the switch structure is at the second position, the carrier gas channel connects through, in the consecutive order, the first purge channel, the seventh port, the eighth port and the first vent channel to the first vent environment, and the carrier gas channel connects through, in the consecutive order, the connecting channel, the second purge channel, the second port, the first port and the second vent channel to the second vent environment.

10. The device according to claim 6, wherein the switch structure comprises a switching valve which comprises a first port, a second port, a third port, a fourth port, a fifth port and a sixth port;
wherein when the switch structure is at the first position, the carrier gas channel connects through, in the consecutive order, the first purge channel, the fifth port, the sample gas channel, the second port and the second purge channel to the output channel; and
wherein when the switch structure is at the second position, the carrier gas channel connects through, in the consecutive order, the first purge channel, the fifth port, the sixth port and the first vent channel to the first vent environment, and the carrier gas channel connects through, in the consecutive order, the connecting channel, the second purge channel, the second port, the first port and the second vent channel to the second vent environment.

11. The device according to claim 6, wherein the switch structure comprises a first pneumatic switch, a second pneumatic switch and a third pneumatic switch;
wherein when the switch structure is at the first position, the carrier gas channel connects through, in the consecutive order, the first purge channel, the second pneumatic switch, the sample gas channel, the third pneumatic switch and the second purge channel to the output channel; and
wherein when the switch structure is at the second position, the carrier gas channel connects through, in the consecutive order, the connecting channel, the second purge channel, the first pneumatic switch and the second vent channel to the second vent environment.

12. The device according to claim 6, wherein the pneumatic restriction of the connecting channel is greater than the sum of the pneumatic restrictions of the first purge channel, the sample gas channel and the second purge channel.

13. An apparatus comprising the device according to claim 6 and an analytical instrument, said analytical instrument connecting to the output channel.

14. The apparatus according to claim 13, wherein the analytical instrument is selected from the group consisting of a gas chromatography, a mass spectrometer and an ion mobility spectrometer.

15. A device, comprising:
an input means for channeling a gas into the device;
an output means for channeling the gas out of the device;
a first purge channel;
a holding means for holding a gaseous sample; and
a switching means for regulating connections among the holding means, the input means and the output means;
wherein the switching means has an open state and a close state;
wherein when the switching means is at the open state, the gas is capable of being channeled from the input means through the holding means and the first purge channel to the output means; and
wherein when the switching means is at the close state, the holding means disconnects to the input means, and the gas is capable of being channeled to (1) a first vent environment through, in the consecutive order, the input means and the first purge channel and (2) the output means through the input means.

16. The device according to claim 15, further comprising:
a second purge channel; and
a connecting means for connecting the input means to the output means;
wherein when the switching means is at the open state, the gas is capable of being channeled through, in the consecutive order, the input meaning, the first purge channel, the holding means and the second purge channel to the output means;
wherein when the switching means is at the close state, the gas is capable of being channeled through, in the consecutive order, the input means, the connecting means and the second purge channel to a second vent environment.

17. The device according to claim 16, wherein the pneumatic restriction of the connecting means is greater than the sum of the pneumatic restrictions of the first purge channel, the holding means and the second purge channel.

18. A device, comprising:
a carrier gas channel;
an output channel;
a first purge channel;
a sample gas channel capable of holding a gaseous sample; and
a switch structure comprising a first switch and a second switch and having at least a first position and a second position;
wherein when the switch structure is at the first position, the carrier gas channel connects through, in the consecutive order, the first switch, the sample gas channel and the second switch to the output channel; and wherein when the switch structure is at the second position, the sample gas channel disconnects to the carrier gas channel, and the carrier gas channel connects to (1) a first vent environment through the first purge channel and (2) the output channel.

19. The device according to claim 18, further comprising:

a second purge channel; and a connecting channel;

wherein the carrier gas channel connects through the connecting channel to the output channel; wherein when the switch structure is at the first position, the carrier gas channel connects through, in the consecutive order, the first purge channel, the first switch, the sample gas channel, the second switch and the second purge channel to the output channel; and wherein when the switch structure is at the second position, the carrier gas channel connects through, in the consecutive order, the connecting channel and the second purge channel to a second vent environment.

20. The device according to claim 19, wherein the switch structure comprises a switching valve which comprises at least a first port and a second port, and wherein the first switch comprises the first port and the second switch comprises the second port.

\* \* \* \* \*